(12) United States Patent
Diez Martin et al.

(10) Patent No.: US 8,962,018 B2
(45) Date of Patent: Feb. 24, 2015

(54) ORAL FORMULATION OF ANHYDROUS OLANZAPINE FORM I

(75) Inventors: Ignacio Diez Martin, Sant Feliu de Llobregat (ES); Carmen Ubeda Perez, Cabrils (ES); Pablo Pablo Alba, Cornella de Llobregat (ES)

(73) Assignee: Laboratorios Lesvi, S.L., Barcelona (ES)

( * ) Notice: Subject to any disclaimer, the term of this patent is extended or adjusted under 35 U.S.C. 154(b) by 1165 days.

(21) Appl. No.: 12/159,030

(22) PCT Filed: Dec. 19, 2006

(86) PCT No.: PCT/EP2006/069905
§ 371 (c)(1),
(2), (4) Date: Jun. 24, 2008

(87) PCT Pub. No.: WO2007/074110
PCT Pub. Date: Jul. 5, 2007

(65) Prior Publication Data
US 2008/0311203 A1    Dec. 18, 2008

Related U.S. Application Data

(60) Provisional application No. 60/754,104, filed on Dec. 27, 2005.

(30) Foreign Application Priority Data

Dec. 26, 2005   (ES) .................................. 200503183

(51) Int. Cl.
*A61K 9/28*   (2006.01)
*A61K 9/36*   (2006.01)
*A61K 31/55*   (2006.01)
*A61K 31/551*  (2006.01)

(52) U.S. Cl.
CPC ............... *A61K 9/284* (2013.01); *A61K 31/551* (2013.01)
USPC ........... 424/464; 424/475; 424/482; 424/474; 424/479; 514/220

(58) Field of Classification Search
None
See application file for complete search history.

(56) References Cited

U.S. PATENT DOCUMENTS

| | | | |
|---|---|---|---|
| 5,703,232 A | 12/1997 | Bunnell et al. | |
| 5,843,477 A * | 12/1998 | Alexander | 424/466 |
| 5,919,485 A * | 7/1999 | Cochran et al. | 424/480 |
| 7,612,112 B2 * | 11/2009 | Berner et al. | 514/561 |
| 7,780,987 B2 * | 8/2010 | Zhou et al. | 424/475 |
| 2001/0018071 A1 | 8/2001 | Cochran et al. | |
| 2005/0272721 A1 | 12/2005 | Keltjens | |

FOREIGN PATENT DOCUMENTS

| | | | |
|---|---|---|---|
| EP | 0830858 A1 * | 3/1998 | |
| WO | 2004/035027 A1 | 4/2004 | |
| WO | 2005/009407 A2 | 2/2005 | |
| WO | 2006/013435 A1 | 2/2006 | |

\* cited by examiner

*Primary Examiner* — Lakshmi Channavajjala
(74) *Attorney, Agent, or Firm* — Cozen O'Connor

(57) ABSTRACT

The invention relates to a solid formulation for the oral administration of olanzapine that comprises a core of anhydrous olanzapine Form I or a pharmaceutically acceptable salt thereof and, optionally, pharmaceutically acceptable excipients, said core being coated with a functional polymer that acts as filmogenic agent. The method for obtaining it comprises: i) providing anhydrous olanzapine Form I or a salt thereof and, optionally, pharmaceutically acceptable excipients in solid form; ii) providing a functional polymer that acts as filmogenic agent; iii) preparing a dispersion of said functional polymer in an aqueous medium,—and applying the dispersion obtained in step iii) onto the solid form of step i).

17 Claims, No Drawings

ORAL FORMULATION OF ANHYDROUS OLANZAPINE FORM I

FIELD OF THE INVENTION

The present invention relates to a new solid formulation for the oral administration of olanzapine or of one of its pharmaceutically acceptable salts.

In particular, the present invention relates to a solid formulation for the oral administration of olanzapine that comprises anhydrous olanzapine Form I or one of the pharmaceutically acceptable salts thereof, as active substance in the core and a functional polymer as coating.

BACKGROUND OF THE INVENTION

Olanzapine is a thienobenzodiazepine of formula (I):

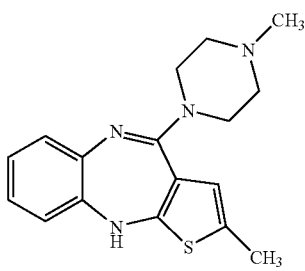 [SMILES: Cc1cc2c(s1)Nc1ccccc1N=C2N1CCN(C)CC1]

that acts as an antagonist on dopamine receptors D1, D2, D3, D4, and D5; of serotonin 5-HT2 and 5-HT3; alpha-1-adrenergics, cholinergics and H1 histaminergics.

Olanzapine is an antipsychotic compound that is marketed in several dosages (2.5, 5, 7.5, 10, 15 mg) for oral administration, or 10 mg for injection for the treatment of schizophrenia, bipolar disorders or manic episodes. However, olanzapine Form I tends to be metastable and to produce an undesirable coloration, while suitable homogeneity of the final solid formulation also has to be ensured.

This coloration arises when certain excipients, including mixtures of powders, come into contact with the olanzapine and increase under ambient environmental conditions of the air, at high temperatures and in wet environments. Although this coloration does not mean an increase in total related substances, it is not acceptable for commercial purposes.

Thus, Spanish patent ES2164837T3 (equivalent to European patent EP 733367) has the object of providing solid oral formulations of olanzapine as active ingredient, thoroughly intermixed with a filler agent, a binder, a disintegrant, a dry binder to ensure appropriate friability and a lubricant; where said solid oral formulation is coated with a polymer selected from among the group that comprises: hydroxypropylmethylcellulose, hydroxyethylcellulose, methylhydroxyethylcellulose, sodium carboxymethylcellulose, hydroxypropylcellulose, polyvinylpyrolidone, copolymer of dimethylaminoethyl methacrylate and methyl acrylate, copolymer of ethyl acrylate and methyl methacrylate, methylcellulose and ethylcellulose, which provides uniformity and physical stability and effectively prevents the phenomenon of undesirable coloration of the formulation.

In particular, said patent precludes the use of a polymer that contains polyethylene glycol. Also according to said patent, it is specially preferred that the formulation contains the most stable anhydrous form of olanzapine referred as Form II. The preferred process described for its preparation is by granulation in aqueous medium.

Moreover, patent application WO04/035027 proposes a highly stable formulation, free from coloration and having good uniformity. In particular, said application describes a formulation that includes a mixture of (a) olanzapine or a salt thereof as active substance; (b) a monosaccharide and/or oligosaccharide; (c) a polysaccharide and, optionally, other ingredients. The preferred oligosaccharide is lactose and the preferred polysaccharide cellulose, and it is preferable for the formulation not to contain microcrystalline cellulose, since this form of cellulose is hygroscopic and can have an adverse effect on the stability of the composition.

In accordance with said document, the phenomenon of coloration is believed to be caused by the formation of hydrates of olanzapine so that, as a consequence, in order to avoid their formation the method for obtaining a formulation that contains olanzapine must be carried out without using solvents. Said formulation is thus prepared by direct compression once the olanzapine or one of its salts has been mixed homogeneously with the excipients mentioned.

Patent application WO05/009407 discloses two ways of preventing the problem of undesirable coloration of formulations containing olanzapine.

In particular, it discloses the coating of particles of olanzapine with lactose and/or mannitol and, optionally, with other pharmaceutically acceptable excipients selected from among at least one binder selected from a polymer of cellulose or polymers of vinylpyrrolidone, at least one disintegrant, at least one filler agent and at least one lubricant. It also proposes coating the tablets of olanzapine with one or more excipients selected from the group that includes carrageenate, sodium alginate, sodium carboxymethylcellulose, a polyvinyl alcohol-polyethylene glycol graft copolymer or a titanium oxide-talc mixture.

The utilisation of polymers insoluble in water that protect the core from moisture has the disadvantage of delaying release of the active substance in the physiological medium. Among them could be cited the use of Shellac (gum-lac) and coatings based on cellulose polymers, such as hydroxypropylmethylcellulose, with stearic acid.

Therefore, there remains to be found a solid formulation for the oral administration of olanzapine that is suitable for commercial utilisation and that permits stabilisation of olanzapine Form I without affecting the bioavailability of the active substance at physiological pH.

BRIEF DESCRIPTION OF THE INVENTION

A first aspect of the present invention is to provide a stable solid formulation for oral administration of anhydrous olanzapine Form I or a pharmaceutically acceptable salt thereof as active substance and, optionally, pharmaceutically acceptable excipients in the tablet core, with said core being coated with a functional polymer that acts as a filmogenic agent.

The authors of the present invention have found surprising effects on the stability of the coloration of the anhydrous olanzapine Form I when the formulation is coated with a polymer having filmogenic properties, in addition to improving the stability of said formulations in the case of excipients of an alkaline nature.

A second aspect of the present invention is to provide a method for preparing a formulation according to the first aspect of the invention.

DETAILED DESCRIPTION OF THE INVENTION

The present invention has the object of solving the problem of coloration of formulations that contain olanzapine by improving their bioavailability in the physiological medium and improving the stability of said formulations by using excipients of an alkaline nature.

With said objective, the present invention provides a solid oral formulation of olanzapine that comprises anhydrous olanzapine Form I or a pharmaceutically acceptable salt thereof as active substance and, optionally, pharmaceutically acceptable excipients in the core, said core being coated with a functional polymer that acts as filmogenic agent.

The authors of the present invention have found that the utilisation of a coating with a functional polymer soluble in aqueous media that acts as a filmogenic agent allows the tablet to have lower permeability to water vapour, thus involving a lower take-up of moisture from the environment, while at the same time the high solubility of the polymer in physiological media leads to suitable release of the active substance without detriment to its bioavailability.

Advantageously, polyvinyl alcohol is preferred as filmogenic agent, although other agents of low permeability to water vapour and high solubility in the physiological medium are also good candidates for use as coating in the formulation of the present invention.

The Form I has an X-ray diffraction pattern characterised by the "°2θ" position, "d" interplanar distances and relative "$I/I_0$" intensities that are included in Table 1 below:

TABLE 1

| Position (°2θ) | d ($m^{-10}$) | $I/I_0$ |
|---|---|---|
| 8.885 | 9.944 | 100 |
| 9.005 | 9.812 | 86 |
| 10.395 | 8.503 | 14 |
| 10.815 | 8.174 | 20 |
| 12.915 | 6.850 | 16 |
| 13.915 | 6.359 | 4 |
| 17.830 | 4.971 | 8 |
| 18.385 | 4.822 | 75 |
| 18.785 | 4.720 | 32 |
| 19.230 | 4.612 | 27 |
| 19.620 | 4.521 | 29 |
| 21.050 | 4.217 | 19 |
| 21.770 | 4.079 | 24 |
| 23.635 | 3.761 | 16 |
| 24.095 | 3.691 | 30 |
| 24.865 | 3.578 | 6 |
| 25.465 | 3.495 | 9 |
| 26.690 | 3.337 | 5 |
| 27.515 | 3.239 | 5 |
| 28.665 | 3.112 | 8 |
| 34.580 | 2.592 | 5 |
| 36.525 | 2.458 | 4 |
| 38.645 | 2.328 | 4 |

Form I can be obtained in accordance with the method disclosed in the Spanish patent application ES200401850 (published as WO2006013435), from the mixed solvate of olanzapine/water/tetrahydrofuran in the proportion 1:1:½.

Said method includes in vacuo drying of the solvate at a pressure ranging between 1 and 40 mmHg, preferably between 1 and 20 mmHg, and a temperature controlled between 10 and 50° C., preferably between 20 and 40° C. Said method provides olanzapine Form I in a simple manner, with a high yield of the end product (olanzapine Form I) and with high chemical purity (level of total impurities less than 0.3% as determined by HPLC), together with a high polymorphic purity (Form II<2%). The Form I product remains stable and does not undergo colour variations under ambient storage conditions.

Surprisingly, it was found that the use of polyvinyl alcohol as filmogenic agent for the coating of tablet cores containing anhydrous olanzapine Form I and pharmaceutically acceptable excipients permits effective coating of the core, improves the stability of the anhydrous olanzapine Form I and prevents or delays the discoloration suffered by pharmaceutical forms that contain olanzapine.

The moisture-isolating properties of the polyvinyl alcohol permit moisture-stable tablets to be obtained that are easily dissolved in aqueous media, thereby permitting release of the active compound. This characteristic assists the dissolution and release of the anhydrous olanzapine Form I in the physiological medium.

Polyvinyl alcohol is a non-toxic synthetic polymer soluble in water, thus making it an appropriate candidate for utilisation in the formulation of the invention.

On the one hand, the coating of the formulation in accordance with the first aspect of the invention can further include one or more of the following excipients: from 10 to 50% of opacifier and colorant, from 5 to 30% of lubricant, from 0.5 to 5% of plasticizer, from 0.1 to 3% of thickening agent and from 0 to 20% of filler agent.

Preferably, the opacifiers and colorants can be selected from: titanium dioxide, calcium carbonate, iron oxides, aluminic lakes or mixtures thereof.

Preferably, the lubricants can be selected from: stearates, sodium benzoate, stearic acid, talc or mixtures thereof.

Preferably, the plasticizers can be selected from: glycerol, polyethylene glycol, sorbitol, soya lecithin, esters of citric acid or mixtures thereof.

Preferably, the thickening agent can be selected from: xanthan gum, bentonite, carrageenates, colloidal silica, ethylcellulose, gelatine, maltitol, sucrose or mixtures thereof.

The core of the formulation in accordance with the first aspect of the invention can contain one or more of the following components: from 20 to 80% of diluent, from 3 to 15% of disintegrant and/or from 0.25 to 5% of lubricant.

In the present invention, "diluent" is taken to mean: saccharides (monosaccharides or oligosaccharides, polysaccharides), and/or their oxidised and/or reduced forms; lactose in its various forms, anhydrous, monohydrate, agglomerated forms or atomised forms; mannitol; cellulose powder, microcrystalline cellulose, silicified microcrystalline cellulose or derivatives of cellulose modified chemically, such as hydroxypropyl cellulose, hydroxypropyl methyl cellulose; starch, sucrose, pharmaceutically acceptable inorganic compounds such as dibasic calcium phosphate, carbonates of calcium or of magnesium, magnesium oxide, or mixtures thereof.

Additionally, coprocessates of diluents can be used, such as Cellactose®, coprocessate of lactose and cellulose powder, or Microcellac®, coprocessate of lactose and microcrystalline cellulose, among others. Here, it is not a simple mixture of two components, since the method of preparation alters the properties of both components, so that it cannot be considered as a mixture.

Preferably, cellulose will be used, more preferably, microcrystalline cellulose or one of its coprocessate forms such as Microcellac®.

In the present invention "disintegrant" is taken to mean: low-substitution hydroxypropyl cellulose, hydroxyethyl cellulose, crospovidone, croscarmellose, starch, sodium starch carboxymethyl, derivatives of casein or mixtures thereof.

In the present invention "lubricant" is taken to mean: magnesium stearate, calcium stearate, glyceryl palmitostearate, talc, stearic acid, glyceryl behenate, sodium lauril sulphate, sodium stearil fumarate or mixtures thereof. Preferably a stearate will be used, and more preferably a magnesium stearate.

Thus the formulation in accordance with the first aspect of the present invention comprises a tablet core of anhydrous olanzapine Form I or a pharmaceutically acceptable salt thereof and, optionally, one or more of the pharmaceutically acceptable excipients mentioned, said core being coated with a filmogenic agent and, optionally, one or more opacifiers, colorants, lubricants, plastifiers, viscosising agents or filler agent.

For its part, the utilisation of a functional coating that acts as filmogenic agent also permits a reduction in the protection and packaging requirements of the tablet, such as for airtight packaging impermeable to water vapour (for example, glass vials) or wrappings (for example, blister packs) that protect the solid form from the environment.

In one embodiment of the present invention a solid oral formulation of olanzapine is provided that comprises anhydrous olanzapine Form I or a pharmaceutically acceptable salt thereof thoroughly mixed with an isolating agent and, optionally, pharmaceutically acceptable excipients in the core.

In particular, anhydrous olanzapine Form I or a pharmaceutically acceptable salt thereof and an isolating agent will be used where the excipients present in the formulation are of an alkaline nature.

The authors of the present invention have found that the utilisation of some excipients, especially those of an alkaline nature such as carbonates and phosphates of alkaline or alkaline-earth metals, can have a negative effect on the chemical stability of the olanzapine if moisture is present in the environment.

Surprisingly, it has been found that the utilisation of an isolating agent of the olanzapine prevents its potential degradation due to the alkaline nature of some excipients. The isolating agent is thoroughly mixed with the active substance, and the rest of the excipients are subsequently added.

The isolating agent can be selected from the group that includes: glyceril palmitostearate, stearic acid, esters or ethers of higher fatty acids or mixtures thereof, although glyceril behenate is preferred.

In accordance with the second aspect of the invention, a method is provided for obtaining said solid formulation for the oral administration of olanzapine defined in claim 1 attached.

The method of preparation of the formulation according to the first aspect of the invention comprises:

i) providing anhydrous olanzapine Form I or a pharmaceutically acceptable salt thereof in solid form and, optionally, pharmaceutically acceptable excipients;

ii) providing a functional polymer that acts as filmogenic agent; iii) preparing a dispersion of said functional polymer in an aqueous medium; and iv) applying the dispersion obtained in step iii) to the solid form of step i).

Surprisingly, it has been observed that the utilisation of an aqueous medium for preparation of the coating does not affect the stability of the solid form, with no increase of related substances nor change in the polymorphic form of the anhydrous olanzapine Form I being detected.

Preferably, said aqueous medium is water. The present invention nevertheless provides for the presence of organic solvents such as short-chain alcohols, for example, methanol, chlorated derivatives such as methylene chloride, acetone or mixtures thereof with water.

As is known, several methods exist for the preparation of solid forms, especially tablets, such as dry granulation, moist granulation or direct compression.

The authors of the present invention have nevertheless found that the best methods for the preparation of tablets that keep the anhydrous olanzapine Form I unaltered and that ensure the uniformity of the tablets are those that avoid the use of solvents.

Preferably, the solid form is a tablet, more preferably still said tablet has been obtained by direct compression or by dry granulation.

The direct compression method consists in making an intimate mixture of the active substance with the excipients in the absence of solvents, and then proceeding to compression. In the method of dry granulation, the procedure is to grind the tablets obtained until a granulate of the desired size has been obtained, which is then compressed again once further excipients have been added to it.

The authors of the present invention have found by means of X-ray diffraction study that the utilisation of a process of direct compression for obtaining tablets of the olanzapine Form I has no effect on the polymorphic form used and, therefore, the Form I remains stable without any formation of detectable amounts of the polymorph Form II being observed.

In one embodiment of the invention, obtaining the solid formulation for the oral administration of anhydrous olanzapine Form I comprises carrying out step i) in two stages:

i-1) preparing a mixture of anhydrous olanzapine Form I or a pharmaceutically acceptable salt thereof with an isolating agent;

i-2) then adding the other excipients to the mixture obtained in stage i-1) and providing a solid form; and proceeding with the remaining steps ii); iii); and iv) described above.

Results

Studies of stability were carried out on samples without additional protection (40° C./75% R.H.), confirming that tablets of olanzapine Form I coated with polymer that acts as filmogenic agent, especially polyvinyl alcohol, are stable for at least one month, without degradation of the product or loss of the physical properties of the tablet (appearance, colour) being observed.

The present invention thus provides a formulation that permits the stabilisation of olanzapine Form I in tablets, through the use of suitable excipients and a coating, preferably with polyvinyl alcohol, that make it suitable for commercial use.

The formulations according to the present invention permit stabilisation of olanzapine Form I without any change being detected into the polymorphic form nor changes of coloration under normal storage conditions, while the polymer used in the coating does not interfere with the bioavailability of the active substance.

There follow some examples which, by way of non-restrictive illustration of the invention, outline preferred embodiments of the various aspects thereof.

EXAMPLES

Olanzapine is marketed in several dosages. The examples offered were carried out with 2.5 mg of olanzapine due to this being the dosage form with least amount of this active substance, which low-dose forms are the ones that present most problems of stability. The required amounts of excipients for compositions with higher amounts of olanzapine (5, 7.5, 10, 15 and 20 mg) will be proportional to the amounts of excipients used in the 2.5 mg dose.

Examples 1 and 2

Olanzapine 2.5 mg Film Coated Tablets

Quantitative Composition Per Tablet:

| Cores: | Example 1 | Example 2 |
|---|---|---|
| 1 Olanzapine Form I | 2.50 mg | 2.50 mg |
| 2 Monohydrate lactose | 60.39 mg | 60.39 mg |
| 3 Microcrystalline Cellulose | 20.14 mg | 20.14 mg |

-continued

| Cores: | Example 1 | Example 2 |
|---|---|---|
| 4 Hydroxypopylcellulose, low-substituted | 3.60 mg | 3.60 mg |
| 5 Crospovidone | 2.70 mg | 2.70 mg |
| 6 Anhydrous colloidal silica | 0.23 mg | 0.23 mg |
| 7 Magnesium Stearate | 0.45 mg | 0.45 mg |
| Coating: | | |
| 8 preparation for coating | — mg | 3.00 mg |

Said preparation for coating is commercially available as Opadry® or can be obtained from a mixture that comprises from 30 to 70% of polyvinyl alcohol, from 10 to 50% of opacifier and colorant such as, for example, titanium dioxide that presents both properties, from 5 to 30% of lubricant such as talc, from 0.5 to 5% of plasticizer such as soya lecithin, and from 0.1 to 3% of thickening agent such as xanthan gum.

Method of Manufacturing:
a) the ingredients 1 to 6 are weighed and sieved through a screen with a mesh size of 0.5 mm.
b) the materials of stage "a" are mixed in a suitable mixture until a homogeneous mixture has been obtained.
c) After weighing and sieving the magnesium stearate through a screen with a mesh size of 0.3 mm, it is incorporated into the homogeneous mixture obtained in section "b", and the whole is mixed for approximately 5 minutes.
d) Compress the mixture of powder obtained in stage "c" in a tableting machine equipped with suitable punches.
e) Shake the coating preparation 8 in order to disperse it in a sufficient amount of purified water to achieve dispersion with a concentration of solids ranging between 5 and 20%, preferably around 8%.
f) Apply the aqueous dispersion obtained in stage "e" onto the tablets obtained in stage "d" by spraying using suitable coating equipment.

Dissolution trials were carried out with tablets of examples 1 and 2 (uncoated tablets and film-coated tablets). The results obtained in the dissolution trials (set out in Table 1) show the similarity of dissolution profiles for the tablets of the two examples, from which it emerges that the presence of coating of film does not alter the release characteristics of the tablets.

Table 2.—Percentages of dissolved dose obtained in the dissolution trials carried out with the tablets of Example 1 (without coating) and Example 2 (coated tablets). Conditions for carrying out trial: equipment, Ph. Eur. paddles at 50 r.p.m., dissolution medium, phosphate buffer solution pH 6.8. The results shown are for a mean of 6 tablets.

TABLE 2

| | Uncoated tablets | | Coated tablets | |
|---|---|---|---|---|
| time (min) | % dissolved | CV % | % dissolved | CV % |
| 15 | 82.08 | 3.11 | 73.70 | 3.58 |
| 30 | 93.12 | 2.49 | 90.08 | 7.20 |
| 60 | 100.00 | 1.79 | 100.00 | 5.45 |

Examples 3 and 4

Olanzapine 2.5 mg film coated tablets

Quantitative Composition Per Tablet

| Cores: | Example 3 | Example 4 |
|---|---|---|
| 1 Olanzapine Form I | 2.50 mg | 2.50 mg |
| 2 Microcrystalline Cellulose | 60.39 mg | 58.37 mg |
| 3 Dihydrated calcium phosphate | 20.14 mg | 19.45 mg |

-continued

| Cores: | Example 3 | Example 4 |
|---|---|---|
| 4 Hydroxypopylcellulose low-substituted | 3.60 mg | 3.60 mg |
| 5 Glyceril behenate | — mg | 2.70 mg |
| 6 Crospovidone | 2.70 mg | 2.70 mg |
| 7 Anhydrous colloidal silica | 0.23 mg | 0.23 mg |
| 8 Magnesium stearate | 0.45 mg | 0.45 mg |
| Coating: | | |
| 8 commercial preparation for coating based on polyvinyl alcohol (Opadry ®) | 3.00 mg | 3.00 mg |

Manufacturing Method:
a) the ingredients 1 to 7 are weighed and sieved through a screen with a mesh size of 0.5 mm.
b) the materials of stage "a" are mixed in a suitable mixer to achieve a homogeneous mixture. In example 4, which also includes glyceril behenate as lubricant, the components 1 and 5 are mixed first, and the remaining materials 2, 3, 4, 6 and 7 are then added.
c) After weighing and sieving the magnesium stearate through a screen with a mesh size of 0.3 mm, it is incorporated into the homogeneous mixture obtained in stage "b" and the whole is mixed for approximately 5 minutes.
d) Compress the mixture of powder obtained in stage "c" in a tableting machine equipped with suitable punches.
e) Disperse the commercial preparation 10 by shaking into a sufficient amount of purified water to achieve a dispersion with a solids concentration of around 8%.
f) Apply the aqueous dispersion obtained in stage "e" onto the tablets obtained in stage "d" by spraying using suitable coating equipment.

The tablets obtained in accordance with examples 3 and 4 described are stored loose, exposed to the environment for one month under the following conditions:
40° C.±2° C./75% R.H.±5% R.H.
50° C.

A determination was made on the tablets at the start and following one month under the conditions described to examine the appearance, with particular attention to coloration, and related substances.

During the monitoring period no sign of discoloration was detected in the tablets, while the results obtained for total related substances are set out in the table below:

| TOTAL RELATED SUBSTANCES | | |
|---|---|---|
| | Example 3 | Example 4 |
| START (recently prepared tablets) | 0.07% | 0.03% |
| 1 month at 40° C. ± 2° C./75% R.H. ± 5% R.H. | 0.46% | 0.28% |
| 1 month at 50° | 0.27% | 0.14% |

Examples 5 and 6

Olanzapine 2.5 mg film coated tablets

Quantitative Composition Per Tablet:

| Tablets | Example 5 | Example 6 |
|---|---|---|
| 1 Olanzapine Form I | 2.50 mg | 2.50 mg |
| 2 Monohydrate lactose | 79.63 mg | — mg |
| 2 Microcrystalline Cellulose | — mg | 40.27 mg |
| 3 Maize starch | — mg | 40.26 mg |

-continued

| Tablets | | Example 5 | Example 6 |
|---|---|---|---|
| 5 | Hydroxypopylcellulose low-substituted | — mg | 3.60 mg |
| 5 | Povidone | 4.50 mg | — mg |
| 6 | Crospovidone | 2.70 mg | 2.70 mg |
| 7 | Anhydrous colloidal silica | 0.23 mg | 0.23 mg |
| 8 | Magnesium stearate | 0.45 mg | 0.45 mg |

Manufacturing Method:

a) The ingredients 1 to 7 are weighed and sieved through a screen with a mesh size of 0.5 mm.

b) the materials of stage "a" are mixed in a suitable mixer to achieve a homogeneous mixture.

c) After weighing and sieving the magnesium stearate through a screen with a mesh size of 0.3 mm, it is incorporated into the homogeneous mixture obtained in section "b" and the whole is mixed for approximately 5 minutes.

d) Compress the mixture of powder obtained in stage "c" in a tabletting machine equipped with suitable punches.

For one half of the tablets so obtained a coating was applied to them based on polyvinyl alcohol as in examples 1 to 4, while the other half of the tablets were left without coating.

The tablets obtained in accordance with examples 5 and 6 described, both film coated and uncoated, were stored loosed, exposed to the environment, for one month under the following conditions: 50° C.

A determination was made on the tablets at the start and following one month under the conditions described to examine the following parameters: appearance, with particular attention to coloration, and total related substances.

At the end of the monitoring period no significant differences were detected in the levels of impurities found for the coated and uncoated tablets, while a change was observed in the appearance of the uncoated tablets, on which an ochre coloration could be clearly discerned, while in the case of the coated tablets no change of appearance was observed.

The invention claimed is:

1. Solid oral formulation of olanzapine in the form of a tablet, characterised in that it comprises a core of anhydrous metastable olanzapine Form I as active substance, wherein the anhydrous metastable olanzapine Form I has the following X-ray diffraction pattern:

| Position (°2θ) | d (m − 1°) |
|---|---|
| 8.885 | 9.944 |
| 9.005 | 9.812 |
| 10.395 | 8.503 |
| 10.815 | 8.174 |
| 12.915 | 6.850 |
| 13.915 | 6.359 |
| 17.830 | 4.971 |
| 18.385 | 4.822 |
| 18.785 | 4.720 |
| 19.230 | 4.612 |
| 19.620 | 4.521 |
| 21.050 | 4.217 |
| 21.770 | 4.079 |
| 23.635 | 3.761 |
| 24.095 | 3.691 |
| 24.865 | 3.578 |
| 25.465 | 3.495 |
| 26.690 | 3.337 |
| 27.515 | 3.239 |
| 28.665 | 3.112 |
| 34.580 | 2.592 |
| 36.525 | 2.458 |
| 38.645 | 2.328 | and pharmaceutically acceptable excipients, wherein said tablet core has been obtained by direct compression or by dry granulation, with said tablet core being coated with an aqueous soluble a functional polymer containing PVA, that acts as filmogenic agent.

2. Formulation according to claim 1, wherein said coating also comprises one or more of the following components: from 10 to 50% of opacifier and colorant, from 5 to 30% of lubricant, from 0.5 to 5% of plasticizer, from 0.1 to 3% of thickening agent and from 0 to 20% of filler agent.

3. Formulation according to claim 2, in which said opacifier and/or colorant is selected from titanium dioxide, calcium carbonate, iron oxides, aluminic lakes or mixtures thereof.

4. Formulation according to claim 2, where said lubricant is selected from stearate, sodium benzoate, stearic acid, talc or mixtures thereof.

5. Formulation according to claim 2, where said plasticizer is selected from glycerol, polyethylene glycol, sorbitol, soya lecithin, esters of citric acid or mixtures thereof.

6. Formulation according to claim 2, where said thickening agent is selected from gum xanthane, bentonite, carrageenates, colloidal silica, ethyl cellulose, gelatin, maltitol, sucrose or mixtures thereof.

7. Formulation according to claim 1, wherein said core further comprises one or more of the following components: from 20 to 80% of diluent, from 3 to 15% of disintegrant and/or from 0.25 to 5% of lubricant.

8. Formulation according to claim 7, where said diluent is selected from saccharides and/or their oxidised and/or reduced forms; lactose in its various forms, anhydrous, monohydrate, agglomerated forms or atomised forms; mannitol; cellulose powder, microcrystalline cellulose, silicified microcrystalline cellulose or derivatives of cellulose modified chemically, such as hydroxypropyl cellulose, hydroxypropyl methyl cellulose; starch, sucrose, pharmaceutically acceptable inorganic compounds, or mixtures thereof.

9. Formulation according to claim 7, where said disintegrant is selected from Low-substituted hydroxypropyl cellulose, hydroxyethyl cellulose, crospovidone, croscarmellose, starch, sodium starch carboxymethyl, derivatives of casein or mixtures thereof.

10. Formulation according to claim 7, where said lubricant is selected from magnesium stearate, calcium stearate, glyceril palmitostearate, talc, stearic acid, glyceril behenate, sodium lauril sulphate, sodium stearil fumarate or mixtures thereof.

11. Formulation according to claim 1, wherein said anhydrous metastable olanzapine Form I is thoroughly mixed with an isolating agent.

12. Formulation according to claim 11, where said isolating agent is selected from glyceril palmitostearate, stearic acid, esters or ethers of higher fatty acids or mixtures thereof.

13. Formulation according to claim 12, where said isolating agent is glyceril behenate.

14. Method for obtaining a formulation in the form of a tablet according to any of the preceding claims, which comprises the steps:

i) providing anhydrous metastable olanzapine Form I and pharmaceutically acceptable excipients in solid form of a tablet by direct compression or by dry granulation;

ii) providing an aqueous soluble function polymer contain PVA that acts as filmogenic agent;

iii) preparing a dispersion of said functional polymer in an aqueous medium; and iv) applying the dispersion obtained in step iii) to the tablet obtained in step i).

15. Method according to claim 14, where said aqueous medium is water.

16. Method according to claim 14, wherein step i) is carried out in two stages:
- i-1) preparing a mixture of anhydrous metastable olanzapine Form I with an isolating agent;
- i-2) then adding the other excipients to the mixture obtained in stage i-1) and providing a tablet; and proceeding with the remaining steps ii); iii); and iv).

17. Method according to claim 16, wherein said isolating agent is selected from: glyceril palmitostearate, stearic acid, esters or ethers of higher fatty acids or mixtures thereof.

* * * * *